United States Patent [19]

Saletan et al.

[11] 4,053,525

[45] Oct. 11, 1977

[54] PROCESS FOR PRODUCTION OF GLYCERINE

[75] Inventors: David I. Saletan, LaPorte; Reginald S. Yeung, Houston; William R. Pledger, Pearland, all of Tex.

[73] Assignee: Shell Oil Company, Houston, Tex.

[21] Appl. No.: 737,627

[22] Filed: Nov. 1, 1976

[51] Int. Cl.$^2$ ............................................ C07C 29/00
[52] U.S. Cl. .................................. 260/635 E; 260/636
[58] Field of Search ............................ 260/636, 635 E

[56] References Cited

U.S. PATENT DOCUMENTS

| | | | |
|---|---|---|---|
| 2,070,990 | 2/1937 | Groll et al. ...................... | 260/635 E |
| 2,605,293 | 7/1952 | Tymstra ................................. | 260/636 |
| 2,838,574 | 6/1958 | Cofer ..................................... | 260/636 |
| 2,873,298 | 2/1959 | Cofer ..................................... | 260/636 |

*Primary Examiner*—Joseph E. Evans
*Attorney, Agent, or Firm*—Al A. Jecminek

[57] ABSTRACT

Chlorohydrin reactant mixtures containing epichlorohydrin and mono- and dichlorohydrins are selectively hydrolyzed to glycerine by contact with an alkali metal carbonate catalyst, preferably sodium carbonate, at a temperature of about 50° to 70° C for a period of from about 20 to about 150 hours in a two phase agitated reaction system comprising an aqueous phase containing at least about 0.5% by weight alkali metal carbonate and an organic solvent phase having less than about 0.5% weight solubility in water and a dielectric constant of less than about 10, said aqueous phase being about 0.5 to about 10 times the volume of the organic solvent phase.

11 Claims, No Drawings

PROCESS FOR PRODUCTION OF GLYCERINE

BACKGROUND OF THE INVENTION

This invention relates to a process for the manufacture of glycerine from mixtures of chlorohydrins. More particularly, this invention is directed to an improved process for alkali metal carbonate catalyzed hydrolysis of chlorohydrin mixtures containing epichlorohydrin and mono and dichlorohydrins wherein a two phase, liquid solvent system is employed in combination with low reaction temperatures to maximize the selectivity with which the mixed chlorohydrin feedstock is converted to glycerine.

It is well known that glycerine can be synthesized by aqueous phase hydrolysis of chlorohydrins with alkali metal carbonate catalysts, e.g., see U.S. Pat. Nos. 2,318,032, 2,810,768 and 2,838,574. While earliest disclosures on this synthetic technique, i.e., U.S. Pat. No. 2,318,032, indicate that the reaction can be carried out over a rather broad temperature range, i.e., 50° to 250° C with a broad variety of chlorohydrin reactants, the thrust of more recent prior art teachings has been in the direction of high reaction temperatures and chlorohydrin reactants made up predominantly, if not exclusively, of epichlorohydrin. In this regard both U.S. Pat. Nos. 2,810,768 and 2,838,574 teach the use of reaction temperatures above 75° C and prefer or specify reaction temperatures which are sufficiently high — i.e., 100° to 200° C in U.S. Pat. No. 2,838,574 and 130° to 200° C in U.S. Pat. No. 2,810,768 — to require the use of a pressurized reaction system. Further, at least U.S. Pat. No. 2,810,768 is limited on its face to the use of a chlorohydrin reactant feedstock made up substantially, if not exclusively, of 1-chloro-2,3-epoxypropane or epichlorohydrin.

The primary benefits of this high reaction temperature hydrolysis are short contact or residence times coupled with a purported high selectivity in the conversion of chlorohydrin reactants to glycerine. However, in practice this high selectivity to glycerine is apparently limited to the use of reactant streams made up substantially of epichlorohydrin in contrast to the glycerol chlorohydrins such as the isomeric dichlorohydrins and monochlorohydrins obtained by conventional chlorohydrination of allyl chloride. In fact, the accepted commercial technique for the conversion of allyl chloride to glycerine typically involves a caustic hydrolysis step after chlorohydrination wherein the glycerol dichlorohydrins are substantially converted to epichlorohydrin with the resultant epichlorohydrin being subject to high temperature carbonate catalyzed hydrolysis to afford glycerine. In this process, the presence of significant amounts of unreacted glycerol chlorohydrins in the epichlorohydrin feed stream to high temperature hydrolysis apparently leads to unwanted side reactions forming heavy ends and difficult to remove by-products which boil near glycerine. While the amount of glycerol chlorohydrins in the epichlorohydrin feed to high temperature hydrolysis can be reduced by recycle of unreacted glycerol chlorohydrins to the chlorohydrin hydrolysis reaction, conventional operation of the process invariably affords one or more waste streams containing glycerol chlorohydrins which must be passed to waste or effluent disposal to avoid the formation of undesirable by-products. These waste streams represent a loss in the overall yield of glycerine from allyl chloride in the process as well as an additional burden on waste treatment facilities.

From the foregoing it is apparent that considerable advantage would be obtained if a chlorohydrin hydrolysis process could be developed in which the full range of possible chlorohydrin reactants including glycerol mono- and dichlorohydrins in addition to epichlorohydrin could be selectively converted to glycerine with a minimum of by-product formation.

SUMMARY OF THE INVENTION

It has now been found that chlorohydrin reactant mixtures containing significant amounts of glycerol mono- and dichlorohydrins in addition to epichlorohydrin can be selectively converted to glycerine by aqueous phase, alkali metal carbonate catalyzed hydrolysis, if the hydrolysis reaction is carried out at a temperature of about 50° to about 70° C in a two phase agitated reaction system comprising an aqueous phase containing at least about 0.5% by weight alkali metal carbonate and an organic solvent phase having less than about 0.5% weight solubility in water and a dielectric constant of less than about 10, said aqueous phase being about 0.5 to about 10 times the volume of the organic solvent phase. The high selectivity with which glycerine is obtained from dichlorohydrin reactant mixtures in the process according to the invention is predicated to a substantial degree on the use of a two phase liquid solvent system wherein one phase is a substantially water immiscible organic solvent of the afore defined critical characteristics. This organic solvent phase, which is in constant and intimate contact with the aqueous phase over the course of the hydrolysis reaction, possesses a high solubility for epoxide-containing starting materials and intermediates in the process, e.g., epichlorohydrin and glycidol, and functions as an extractant for said epoxides in the process, thereby minimizing their contact with the more water soluble hydroxyl compounds such as the glycerol chlorohydrins which are present substantially in the aqueous phase during the hydrolysis process. As a result, the epoxide compounds are made slowly available to the reactive, catalyst containing phase during the course of the reaction, and unwanted side-reactions between the epoxide-containing compounds and hydroxyl compounds in the aqueous reaction phase are reduced. The advantageous effects of the unique two phase solvent system according to the invention on chlorohydrin reactant selectivity to glycerine are further optimized by the use of the low reaction temperature range specified for the invention. With this low reaction temperature range, it is now possible to obtain glycerine in high selectivity without the need for the pressurized reaction system which characterizes the high temperature hydrolysis process of the prior art. Additionally, the use of low reaction temperatures coupled with longer residence times provides an opportunity for stages addition of different chlorohydrin-containing reactant steams based on the decreasing chlorine content of the glycerine precursors as a means of further maximizing reactant selectivity to glycerine in a way which is not feasible with the short residence time, high temperature hydrolysis processes of the prior art. In this preferred aspect of the invention, which is particularly applicable to the conversion of various chlorohydrin-containing waste streams from conventional manufacture of epichlorohydrin to glycerine, the chlorohydrin-containing streams where the glycerine precursors having the highest chlorine contents are added first to the hydrolysis reaction.

DESCRIPTION OF THE PREFERRED EMBODIMENTS

The process of the invention is broadly applicable to the production of glycerine in high yield and selectivity from any chlorohydrin feedstock of mixed composition wherein both hydroxy-containing compounds, i.e., glycerol mono- and dichlorohydrins and epoxide-containing precursors—i.e., epichlorohydrin and, optionally, glycidol—are present in significant quantities. Suitable mixed chlorohydrin feedstocks include mixtures of epichlorohydrin and mono- and dichlorohydrins such as those obtained by conventional chlorohydrination of allyl chloride and subsequent caustic hydrolysis of at least a portion of the resultant glycerol dichlorohydrins to epichlorohydrin. In this preparative scheme, any glycerol monochlorohydrin present is largely a result of nucleophilic substitution of water on the epichlorohydrin formed in the caustic hydrolysis reaction. Typically, the mixed chlorohydrin feedstocks which are suitable for use as reactants in the process of the invention contain about 50 to about 100% by weight glycerol chlorohydrins including the isomeric dichlorohydrins 2,3-dichloro-1-propanol and 1,3-dichloro-2-propanol and the monochlorohydrin, 3-chloro-1,2-propandiol, and about 0 to about 50% by weight epichlorohydrin based on the total weight of chlorohydrins present. One of the primary advantages of the process of the invention over conventional high temperatures hydrolysis processes is the ability to afford very selective conversion of chlorohydrin precursors to glycerine when low levels of epichlorohydrin and correspondingly higher levels of dichlorohydrins are present in the reactant mixtures. In conventional high temperature hydrolysis processes, it is generally required that at least 60% by weight of the chlorohydrins in the reactant feedstock be in the form of epichlorohydrin to avoid undue by-product make in the glycerine product, whereas with the present invention such by-product formation is minimized by partitioning of the potential by-product forming reactants into different solvent phases in the reaction system. Under these circumstances, it is preferred that the chlorohydrin reactant mixture employed in the process of the invention contain no more than about 20% by weight epichlorohydrin based on the total weight of chlorohydrins present. In its most preferred application, the process of the invention is employed to produce glycerine from the various chlorohydrin-containing waste or by-product streams obtained in conventional manufacture of epichlorohydrin from allyl chloride. These chlorohydrin-containing waste streams originate from various process operations in the process sequence—e.g., aqueous and organic waste streams from epichlorohydrin purification and storage, etc.— and typically containing varying amounts of epichlorohydrin and glycerol chlorohydrins as well as water and/or other organic by-products—e.g., trichloropropane, bisdichloropropyl ethers and the like. As a general matter, the combined chlorohydrin-containing waste effluent from this conventional epichlorohydrin manufacturing process contains from about 2 to 20% weight epichlorohydrin and about 80 to 98% weight glycerol dichlorohydrins based on total chlorohydrin content and, as such, is unsuitable for high temperature hydrolysis without additional epichlorhydrin fortification. In the process according to the invention, this combined waste stream can be readily converted to glycerine in high selectivity and yield. When the process of the invention is employed to recover glycerine from chlorohydrin-containing waste streams according to this preferred aspect, the reactant conversion to glycerine is optimized by staged addition of the various by-product streams to the hydrolysis process with the sequence of reactant addition being dependent on the relative level of chlorine in the glycerine precursor being added. Specifically, the reactant streams with the highest chlorine contents are added initially with the remaining precursor streams being added sequentially in an order of decreasing chlorine content.

According to the invention it is essential that the chlorohydrin hydrolysis reaction be carried out in a two phase, agitated reaction system comprising an aqueous phase containing at least about 0.5% by weight alkali metal carbonate catalyst and an organic solvent phase having less than about 0.5% weight solubility in water and a dielectric constant of less than about 10. In this reaction system made up of two substantially immiscible liquid phases, the hydrolysis reactions occur in the catalyst-containing aqueous phase which also functions as solvent for the glycerol chlorohydrins present and the glycerine formed by hydrolysis. While any alkali metal carbonate is effective in catalyzing the hydrolysis reaction according to the invention, practical considerations such as availability and cost favor the use of sodium or potassium carbonate with sodium carbonate being the most preferred. During the course of the hydrolysis, the carbonate catalyst reacts to form an alkali metal bicarbonate and the corresponding chloride salt, i.e., the sodium carbonate catalyst is converted to sodium chloride and sodium bicarbonate. The presence of significant amounts of alkali metal bicarbonate in the aqueous phase of the hydrolysis reaction system can be tolerated. However, the bicarbonate concentration should not be allowed to build up at the expense of dropping the carbonate concentration below the above defined limit. In accordance with the invention, the concentration of alkali metal carbonate, e.g., sodium carbonate, in the aqueous phase is suitably controlled above this minimum adding the corresponding alkali metal hydroxide, e.g., sodium hydroxide, to the reaction mixture. Any excess of alkali metal hydroxide over that required to convert bicarbonate into carbonate can have an adverse effect on the selectivity with which chlorohydrin reactants are converted to glycerine in the process. Therefore, for example, when sodium carbonate is employed as the hydrolsis catalyst, it is preferred that the concentration of sodium bicarbonate be controlled via addition of sodium hydroxide at a level between about 1% and about 5% by weight during the hydrolysis reaction. Preferably the sodium carbonate catalyst concentration is maintained at a level of at least 2% by weight of the aqueous phase during the hydrolysis reaction. In principle, there is no upper limit for the alkali metal carbonate catalyst concentration in the process according to the invention other than that dictated by practical considerations such as solubility. As a general matter, a high initial concentration of alkali metal carbonate, for example, 20% by weight of the aqueous phase, is employed which declines with neutralization and dilution to a level above 0.5% by weight, typically about 2% by weight of the aqueous phase, as the hydrolysis reaction goes to completion.

The nature of the organic solvent employed in the two phase reaction system of the invention is especially critical to the high selectivities obtained with the process according to the invention. This organic solvent functions primarily as an extractant for any epichlorohydrin reactant added to, or intermediate formed in, the hydrolysis reaction, thereby limiting the contact between epichlorohydrin and the more water soluble glycerol chlorohydrins during the hydrolysis reaction, which, in turn, reduces unwanted side-reactions between the epoxide group and hydroxyl compounds in the aqueous reaction phase. Over the course of the hydrolysis reaction, this organic solvent phase slowly releases the epoxide compound to the aqueous reaction phase at a controlled rate sufficient to promote selective hydrolysis of the contained epichlorohydrin and glycidol reaction intermediates. In accordance with the invention, this organic solvent phase has less than about 0.5% by weight solubility in water and a dielectric constant of less than about 10. Preferably, the organic solvent employed has a low vapor pressure at the reaction temperatures—i.e., less than 10 psia at 70° C. Suitable organic solvents, which provide substantially non-volatile liquid phases at the contemplated reaction temperatures, include aromatic hydrocarbons such as toluene and xylene, aliphatic hydrocarbons such as octane and nonane as well as a variety of substituted aromatic and aliphatic hydrocarbons such as chlorobenzene, p-chlorotoluene, tetrachloroethane, isopropyl ether, and phenyl ether. Preferred organic solvents are chlorinated aliphatic hydrocarbons of 3 to 6 carbon atoms substituted with up to 6 chlorine atoms. Mixtures of various organic solvents may be employed. A particularly preferred solvent is trichloropropane which occurs as a by-product of conventional chlorohydrination of allyl chloride in the process for manufacture of epichlorohydrin from allyl chloride. This by-product trichloropropane is generally obtained as a bottoms product of a distillation used to purify epichlorohydrin and, as such, it contains minor amounts of other organic impurities i.e., bisdichloropropyl ethers, as well as appreciable amounts of glycerol chlorohydrins, e.g., up to 45% by weight, and epichlorohydrin, e.g., up to 10% by weight. The use of this by-product trichloropropane containing appreciable concentrations of intermediates susceptible to hydrolysis to glycerine provides a convenient way of recovering glycerine from precursors which would otherwise be a source of waste from the epichlorohydrin manufacturing process.

To insure the desired partitioning of epichlorohydrin and glycerol chlorohydrins between the organic and aqueous phases, respectively, in the hydrolysis reaction of the invention, it is necessary to control the relative volumes of the two liquid solvent phases within certain limits. As a general matter, the volume ratio of solvent phases should be controlled so that the aqueous phase is about 0.5 to about 10 times the volume of the organic phase in the hydrolysis reaction zone. Preferably, this volume ratio is controlled such that the aqueous phase is 1 to 5 times the volume of the organic phase. It is also desirable to provide a sufficient volume in the combined solvent phases so that the concentration of glycerine precursors or product glycerine does not exceed about 20% by weight of the combined solvent phases. Preferably, the quantities of chlorohydrin reactant mixture and solvent phases are controlled such that between about 5 and about 15% by weight glycerine is present in the aqueous phase upon completion of the hydrolysis, if complete reactant conversion to glycerine is assumed.

The selective hydrolysis according to the invention is carried out at a reaction temperature between about 50° and about 70° C. When the process is carried out in a batch system, it is desirable to initiate the hydrolysis reaction at a temperature at the low end of this reaction temperature range e.g., at about 50° C, followed by a slow rise in reaction temperature as the hydrolysis reaction goes to completion until a final temperature is reached at the upper end of the range i.e., about 70° C. Since the reaction is exothermic, this temperature control can be achieved primarily through control of external coolant provided to the reaction zone. The reaction residence time required for high reactant conversions is a function of a variety of process parameters such as the initial concentration of reactants, the chemical make up of the reactant mixture employed, the operating temperature, concentration of alkali metal carbonate catalyst and the degree of mixing. In practice, these process parameters can be readily manipulated to afford substantially complete reactant conversion in residence times of from about 20 to about 150 hours. Preferably the reaction time is less than 150 hours and most preferably betweem about 36 and about 100 hours. At the reaction temperatures employed, the hydrolysis reaction can be carried out at substantially atmospheric pressures.

Various procedures can be used in carrying out the process according to the invention. It can be conducted batchwise, intermittently or continuously. In continuous operations, the process of the invention can be suitably carried out by continuously charging the chlorohydrin reactant mixture and solvent phases cocurrently to an agitated reaction zone e.g., unpacked vessel or tubular reactor, which is sized sufficient to provide the desired residence time for complete reactant conversion. In this continuous system, a recycle loop can be employed to increase the contact between the phases and uniformity of composition in the phases. Glycerine can be recovered in this continuous system by passing the reaction zone effluent to a continuous phase separation vessel where the glycerine-containing aqueous phase is separated and passed to product purification. The organic solvent phase which separates in this convention phase separation is suitably recycled to the hydrolysis reaction zone on a continuous basis. Preferably, the reaction is conducted using a batch technique. With this preferred procedure, predetermined amounts of chlorohydrin reactant mixture, catalyst-containing aqueous solvent and organic solvent are charged to an agitated reaction vessel which is conveniently sized to accomodate large batches of reactant mixture. After the appropriate residence time to afford complete reactant conversion to glycerine, agitation is terminated and the contents of the batch reactor are allowed to phase separate under quiescent conditions. After phase separation the aqueous phase containing the product glycerine is passed to product recovery and, if desired, all or substantially all of the remaining organic solvent phase can be reused in subsequent batch hydrolysis reactions. This batch hydrolysis technique is especially advantageous in that it provides a ready means of staging the reactant addition to the hydrolysis reaction according to a preferred embodiment of the invention, discussed above, where various chlorohydrin-containing waste streams with reactants of differing chlorine content are subject to hydrolysis. In this preferred embodiment when the batch hydrolysis technique is employed to recover glycerine from various chlorohydrin-containing waste streams from the conventional process for conversion of allyl chloride to epichlorohydrin, the batch reactor is suitably first charged with the aqueous phase containing alkali metal carbonate catalyst, e.g., 20% by weight sodium carbonate, and the trichloropropane organic solvent phase, recovered as a by product of epichlorohydrin purification. After initiation of the reaction, other chlorohydrin-containing waste streams are added in ordered sequence based on decreasing chlorine content of the contained glycerine precursors. The chlorohydrin-containing waste streams added subsequently will generally be aqueous-based streams and, as a result, a certain further dilution of the reactants and reaction product in the reaction zone will occur. According to this preferred embodiment, it is desirable to select a reactor volume, reactant concentration and reaction solvent phase ratio so that the concentration of glycerine in the aqueous phase of the reaction mixture is between about 5 and about 15% by weight upon completion of the hydrolysis reaction.

By carrying out the chlorohydrin hydrolysis reaction in accordance with the invention, it is possible to achieve selectivities to glycerine in excess of 90% based on total chlorohydrin reactants charged at reactant conversions approaching 100%. This glycerine product, obtained as an aqueous solution on completion of the hydrolysis, is of high purity, containing a minimum amount of diglycerol ethers and related compounds, and can be readily purified into a product grade acceptable for commerce by conventional techniques.

ILLUSTRATIVE EMBODIMENT

To demonstrate the process of the invention, a plant scale test was carried out, in which typical chlorohydrin-containing waste streams from a conventional process for the production of epichlorohydrin from allyl chloride were subject to sodium carbonate catalyzed hydrolysis in the two-phase liquid solvent system of the invention. The organic solvent employed in this test was the trichloropropane-containing by-product of the epichlorohydrin manufacturing process obtained as a bottoms product of crude epichlorohydrin distillation. The reaction was conducted batchwise in a 70,000 gas vessel equipped with 10 eductors on a recirculation line to maintain agitation during the reaction period. The initial charge to the reaction vessel included 13,700 gal of organic solvent (by-product trichloropropane), 15,700 gal of 16% by weight aqueous sodium carbonate solution. The reaction initiated at a temperature of 50° C and carried out over a total residence time of 90 hours in which the reaction temperature was raised slowly to a final temperature of 66° C. During the course of the reaction period, the sodium bicarbonate concentration in the aqueous phase was controlled at 5% by weight or less by the incremental addition of 11,000 gal of 25% aqueous sodium hydroxide. Additional aqueous chlorohydrin-containing waste (26,600 gal total) during the first 24 hours after the reaction was initiated. The aqueous and organic solvent phases were analyzed at 3, 20, 44, 66, and 90 hours into the reaction period to determine the concentration of chlorohydrin reactants present and the extent to which the reactants had been converted to glycerine by the process. The results of the plant test are given in the table below. This table details the compositional analysis of the aqueous and organic solvent phases at the time periods indicated as well as the chemical make up of the trichloropropane solvent charge and chlorohydrin-containing reactant charges. Based on the quantities of reactants charged and the chemical analysis given in the Table it has been determined that 99% of the chlorohydrin reactants charged under went hydrolytic conversion to afford glycerine in a selectivity of 93%. In the table below, the following abbreviations are used:

ECH — Epichlorohydrin
DCH — Dichlorohydrin
MCH — Monochlorohydrin
TCP — Trichloropropane.

TABLE

| Component | Quantity (Gal) | Composition, %w | | | |
|---|---|---|---|---|---|
| | | Na$_2$CO$_3$ | NaHCO$_3$ | ECH | 1,3-DCH |
| Initial Charge | | | | | |
| Organic Solvent | 13,700 | | | 0.8 | 7.3 |
| Carbonate Solution | 15,700 | 16.6 | | | |
| Subsequent Additions | | | | | |
| Aqueous Chlorohydrins | 1,800 | | | | 0.8 |
| Aqueous Chlorohydrins | 8,100 | | | | 0.9 |
| Aqueous Chlorohydrins | 16,700 | | | 0.3 | 0.9 |
| 25% NaOH | 11,000 | | | | |
| Reaction Hours | Phase | | | | |
| 3 | Aqueous | | | 0.09 | 0.08 |
| | Organic | | | 4.5 | 1.6 |
| 20 | Aqueous | 0.6 | 3.9 | 0.07 | 0.4 |
| | Organic | | | 2.2 | 1.4 |
| 44 | Aqueous | 0.5 | 3.3 | 0.03 | 0.3 |
| | Organic | | | 1.7 | 0.5 |
| 66 | Aqueous | 2.5 | 1.2 | 0.01 | 0.1 |
| | Organic | | | 0.3 | 0.3 |
| 90 | Aqueous | 2.7 | 1.0 | <0.01 | <0.01 |
| | Organic | | | 0.1 | |

| Component | Composition, %w | | | |
|---|---|---|---|---|
| | 1,2-DCH | MCH | TCP | Glycerine |
| Initial Charge | | | | |
| Organic Solvent | 19.0 | 10.6 | 51.1 | |
| Carbonate Solution | | | | |
| Subsequent Additions | | | | |
| Aqueous Chlorohydrins | 1.3 | 4.9 | | 1.1 |
| Aqueous Chlroohydrins | 1.6 | 6.1 | | 1.6 |
| Aqueous Chlorohydrins | 3.2 | 1.9 | | |
| 25% NaOH | | | | |
| Reaction Hours | Phase | | | |

TABLE-continued

| | | | | | |
|---|---|---|---|---|---|
| 3 | Aqueous | 1.5 | 0.9 | | |
| | Organic | 19.2 | | 57.0 | |
| 20 | Aqueous | 2.2 | 0.8 | | |
| | Organic | 14.9 | | 61.0 | |
| 44 | Aqueous | 1.6 | 0.2 | | 8.9 |
| | Organic | 8.6 | | 67.5 | |
| 66 | Aqueous | 0.2 | 0.02 | | 10.3 |
| | Organic | 1.5 | | 75.1 | |
| 90 | Aqueous | <0.01 | <0.01 | | 10.3 |
| | Organic | 0.3 | | 77.1 | |

What is claimed is:

1. A process for the production of glycerine from a chlorohydrin reactant mixture containing epichlorohydrin and glycerol mono- and dichlorohydrins which comprises hydrolyzing the chlorohydrin reactant mixture at a temperature of about 50° to about 70° C by contact with an aqueous phase containing at least 0.5% by weight alkali metal carbonate catalyst in the presence of an organic solvent phase having less than about 0.5% weight solubility in water and a dielectric constant of less than about 10, said aqueous phase being about 0.5 to about 10 times the volume of the organic solvent phase, for a period of from about 20 to about 150 hours.

2. The process according to claim 1 wherein the alkali metal carbonate catalyst is sodium carbonate.

3. The process according to claim 2, wherein the chlorohydrin reactant mixture contains about 50 to 100% by weight glycerol mono and dichlorohydrins and about 0 to about 50% by weight epichlorohydrin based on the total weight of chlorohydrin present.

4. The process according to claim 3 wherein the chlorohydrin reactant mixture is made up substantially of chlorohydrins contained in waste effluents from the process for manufacture of epichlorohydrin by chlorohydrination of allyl chloride and subsequent caustic hydrolysis of the chlorohydrin product to epichlorohydrin.

5. The process according to claim 4 wherein the chlorohydrin reactant mixture contains from about 2 to about 20 epichlorohydrin and from about 80 to about 98% glycerol dichlorohydrins based on the total weight of chlorohydrins present.

6. The process according to claim 2, wherein the organic solvent is trichloropropane.

7. The process according to claim 6 wherein the trichloropropane is obtained as a bottoms product of a distillation used to purify epichlorohydrin in the process for production of epichlorohydrin from allyl chloride by chlorohydrination and subsequent caustic hydrolysis.

8. The process according to claim 7, wherein the trichloropropane contains up to 50% by weight of glycerol chlorohydrins and up to 10% by weight epichlorohydrin.

9. The process according to claim 8 wherein the hydrolysis reaction is carried out batchwise.

10. The process according to claim 9, wherein the chlorohydrin reactant mixture is made up substantially of chlorohydrins contained in waste effluents from the process for manufacture of epichlorohydrin by chlorohydrinatin of allyl chloride and subsequent caustic hydrolysis of the chlorohydrin product to epichlorohydrin.

11. The process according to claim 10, wherein the chlorohydrin-containing waste effluents are added in ordered sequence to the hydrolysis reaction based on decreasing chlorine content of the chlorohydrin reactant mixture with the waste effluent containing the highest level of chlorine being added first.

* * * * *